United States Patent
Brownscombe et al.

(10) Patent No.: US 6,316,665 B1
(45) Date of Patent: Nov. 13, 2001

(54) PROCESS FOR PRODUCING DIACIDS BY CARBOXYLATION OF PHENOLIC COMPOUNDS

(75) Inventors: Thomas Fairchild Brownscombe, Houston, TX (US); Garo Vaporciyan, Amsterdam (NL); Narayana Mysore; Susan Secor Pfrehm, both of Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/643,519

(22) Filed: Aug. 22, 2000

Related U.S. Application Data

(60) Provisional application No. 60/151,490, filed on Aug. 30, 1999.

(51) Int. Cl.⁷ .......................... C07C 63/00; C07C 63/33; C07C 63/337; C07C 63/44; C07C 63/64
(52) U.S. Cl. .......................... 562/405; 562/424; 562/467; 562/468; 562/425
(58) Field of Search ................... 562/405, 424, 562/467, 468, 425

(56) References Cited

U.S. PATENT DOCUMENTS

| | | | |
|---|---|---|---|
| 2,833,816 | 5/1958 | Saffer et al. | 260/524 |
| 3,856,855 | 12/1974 | Yamashita et al. | 260/524 R |
| 3,870,754 | 3/1975 | Yamashita et al. | 260/524 R |
| 4,933,491 | 6/1990 | Albertins | 562/416 |
| 4,950,786 | 8/1990 | Sanchez et al. | 562/416 |
| 5,292,934 | 3/1994 | Sikkenga et al. | 562/413 |

OTHER PUBLICATIONS

Gore et al, Indian Journal of Chemistry, vol. 12, 1974, pp. 946 to 947.*
Chen et al, Organic Preparations and Procedures Int., vol. 31 (1), 1999, pp. 106–109.*

\* cited by examiner

Primary Examiner—Gary Geist
Assistant Examiner—Hector M Reyes
(74) Attorney, Agent, or Firm—Kim Muller

(57) ABSTRACT

An oxidation free process for converting a hydroxy substituted aromatic to an aromatic diacid which comprises reacting a hydroxy substituted aromatic with excess basic salt in the presence of carbon dioxide at disproportionation/isomerization reaction conditions.

15 Claims, No Drawings

PROCESS FOR PRODUCING DIACIDS BY CARBOXYLATION OF PHENOLIC COMPOUNDS

This application claims the benefit of U.S. Provisional Application No. 60/151,490, filed Aug. 30, 1999, the entire disclosure of which is hereby incorporated by reference

FIELD OF INVENTION

This invention relates to the production of valuable diacids, such as terephthalic acid and 2,6-naphthalene dicarboxylic acid, by a novel reaction, the conversion of a phenolic compound, such as phenol or naphthol, to terephthalic acid or naphthalene dicarboxylic acid, respectively, by the action of high temperature and base. This invention provides a novel non-oxidative route from a low cost raw material to very valuable products that are of exceptionally high purity.

BACKGROUND OF THE INVENTION

It is well known in the art that aromatic carboxylic acids, as the potassium salts, can be isomerized or disproportionated via the Henkel reaction to form aromatic para substituted diacids. In this way, phthalic acid salts or benzoic salts, for example, can be made into terephthalic acid salts (TPA salts) and naphthoic acid salts or other isomers of naphthalene dicarboxylic acid (NDA) may be made into 2,6-naphthalene dicarboxylic acid (2,6-NDA). These compounds are often used as monomers for the preparation of polymeric materials. 2,6-naphthalene dicarboxylic acid (2,6-NDA) is a particularly useful aromatic carboxylic acid, because it can be reacted with ethylene glycol to prepare poly(ethylene-2,6-naphthalate), PEN.

The reaction of phenol with base to form salicylic acid at ca. 150–200° C. with a $Na^+$ counter ion by the addition of $CO_2$, or parahydroxy benzoic acid at high temperature (225–300° C. with $K^+$ counter ion) is known in the literature, but it has never been observed that terephthalic acid (TPA) could be produced by either reaction. Neither has anything been found in the art to suggest that phenols could be useful to the Henkel reaction.

There is nothing found in the art to suggest that terephthalic acid could be produced directly from phenol, or that naphthalene dicarboxylic acid could be produced directly from naphthol. It would be of great value in the art if reactions such as this were possible, because phenol and naphthol are quite inexpensive as raw materials. Phenol can be prepared extremely inexpensively, at about one-third the cost of benzoic acid. Likewise, naphthol is readily available from naphthalene, for example by sulfonation or sulfation followed by hydrolysis, without the use of the oxidation reactions needed to form naphthalene dicarboxylic acid or naphthoic acid from hydrocarbons.

In addition, it would be very advantageous if a reaction to produce valuable diacids could be carried out without an oxidation step. A process that does not require oxidation could obviate the necessity of air separation plants, thus lessening the required scale for economic feasibility. It would be very desirable if there were a safe, oxidation-free route from common precursors, such as phenolic compounds, to desired diacid monomers for polyesters.

In the present invention, we have discovered a novel reaction comprising the conversion of phenolic compounds to diacids by the action of high temperature and base. Since the diacid products are of exceptionally high quality, the process is therefore a convenient way to make a high value product from a low cost raw material by a non-oxidative route.

SUMMARY

In accordance with the foregoing the present invention comprises an oxidation free process for converting a hydroxy substituted aromatic, or salt thereof, to an aromatic diacid which comprises reacting said hydroxy substituted aromatic with excess base in the presence of carbon dioxide at disproportionation/isomerization reaction conditions.

In a preferred embodiment, for example, an alkali metal salt of phenol is heated with excess potassium carbonate base in the presence of a disproportionation catalyst at a temperature in the range of 400–500° C. and a carbon dioxide pressure of 100 to 500 psig for 1–3 hours.

DETAILED DESCRIPTION OF THE INVENTION

The process of the present invention comprises heating an aromatic hydroxy compound, preferably a phenolic compound or an alkaline metal or alkaline earth metal salt of a phenolic compound, with excess base, such as, for example, potassium carbonate, or Group IB or IIB salts, in the presence of at least an atmosphere of carbon dioxide at temperatures above about 350° C., and optionally in the presence of a metal catalyst. Other basic salts, such as, for example an oxalate, may further increase the rate of reaction, but may also add to the cost, and are not critical.

Instead of an oxidative process, this process involves the direct addition of carbon dioxide to the aromatic groups. Thus, almost one-half the weight of the product comes from carbon dioxide (at 0.5 cpp) while about one-half the weight comes from the hydroxy substituted aromatic, for example, phenol, at 15–25 cpp. Therefore, the present invention represents a low raw material cost, non-oxidative route to exceptionally high purity terephthalic acid.

The basic process is applicable to a broad range of aromatics since the reaction site involves the hydroxyl group bonded to a benzene ring. The rest of the hydroxy aromatic can be anything as long as it does not contain other substituents which would interfere with the course of the reaction, for example, by reacting with the carbon dioxide. The aryl portion of the molecule may be a mono-, di- or tri-nuclear radical, or for that matter, can contain even more aryl groups. The aryl portion of the hydroxy aromatic may also be fused to other cyclic systems including heterocyclic systems, such as those containing cyclo oxygen, nitrogen and sulfur rings. For example, the hydroxy aromatic can be any of the isomeric hydroxysubstituted derivatives of benzene, naphthalene, anthracene, phenanthrene, indene, isoindene, benzofuran, isobenzofuran, indole, 1,2-benzopyran, quinoline, isoquinoline, acenaphthene, fluorene, dibenzopyrrole, xanthene, thianthrene, naphthacene, chrysene, pyrene, triphenylene, and the like, wherein the hydroxyl group is bonded to a nuclear carbon atom.

The process is also applicable to aryl hydroxy compounds having more than one hydroxyl radical bonded to a nuclear aromatic carbon atom. For example, the process can be applied to such polyhydroxy aromatics such as hydroquinones, resorcinols, catechols, 1,3-dihydroxy naphthalenes, pyrogallols, phloroglucinols, and the like.

Substituents other than hydroxyl groups may be present in the aromatic compounds as long as they do not interfere with the course of the reaction. That is to say, the other substituents should be relatively inert to carbon dioxide and should not act to poison the catalyst. For example, any of the previously-listed aromatics may be substituted in a variety of positions with alkyl radicals, aralkyl radicals, cycloalkyl radicals, and the like.

The reaction proceeds very satisfactorily when the hydroxy aromatic is phenol or naphthol. It is advantageous to use the hydroxy-containing aromatics in the form of an alkali metal salt. Preferably the potassium salts or the sodium salts are used. The rubidium and cesium salts, may be used, but generally are not for reasons of economy. It is also possible to use mixtures of salts of two different metals. Reaction materials that form the above-mentioned salts may also be used.

Suitable bases include carbonates, oxalates, hydroxides, formates, peroxides, oxides, and related materials. Preferred bases are alkali metal carbonates and bicarbonates. The alkali metal can be selected from the group consisting of lithium, sodium, potassium, rubidium, and cesium, but is preferably potassium. Bases which can be used to provide the excess include, but are not limited to, $K_2CO_3$, $KHCO_3$, $Rb_2CO_3$, $RbHCO_3$, $Cs_2CO_3$, $CsHCO_3$, and other strongly basic carbonates or bicarbonates. We have found it advantageous to use potassium carbonate or potassium bicarbonate. Potassium hydroxide will work, but for the purposes of the present invention, carbonates and bicarbonates are preferred.

An excess of base is an important element of the present invention. An excess of base to hydroxy substituted aromatic in the range of 0.01 to 10.00 is within the inventive concept. The benefits of the excess base are accomplished within the range of 0.2 to 3.0, preferably 1.0 to 2.0, equivalents of base to hydroxy substituted aromatic; and it is believed that, generally, about 2.0 to 3.0 equivalents of base to, for example, phenol, will ensure reproducible results.

Any catalyst that can be used for disproportionation, such as, for example, in the Henkel process could be used in the process of the present invention. Suitable catalysts can be selected from compounds of Group IB, IIB, VB, or VIIB of the Periodic Table. Generally, a suitable catalyst would be selected from zinc compounds, cadmium compounds, and mercury compounds in the form of, for example, oxides, halides, sulfates, carbonates, and carboxylates of these metals.

In the present process a zinc compound is preferred. Suitable zinc compounds include zinc halides such as zinc fluoride, zinc chloride, zinc bromide, and zinc iodide; zinc carboxylates such as zinc naphthoate and zinc naphthalenedicarboxylate; zinc oxide, zinc carbonate; zinc sulfate and mixtures thereof. Note zinc naphthoate includes a 1-isomer, a 2-isomer, and mixtures thereof, and zinc naphthalene dicarboxylate includes a 1,2-isomer, a 1,3-isomer, a 1,4-isomer, a 1,5-isomer, a 1,6-isomer, a 1,7-isomer, a 1,8-isomer, a 2,3-isomer, a 2,6-isomer, a 2,7-isomer, and mixtures thereof. Where a catalyst was employed it was preferably ZnO.

Suitable temperatures for the disproportionation reaction are in the range of from about 340° C. to 520° C. Better results are observed where the temperature is from about 400° C. to 500° C. The preferred temperature is from about 440° C. to 480° C. At 450° C. TPA was observed as noted in Examples 1 and 2.

The disproportionation reaction is carried out under the pressure of gaseous carbon dioxide. The gaseous mixture may contain an inert gas or gases such as nitrogen, methane, or other gaseous paraffinic, olefinic, and aromatic hydrocarbons. In the case of a gas mixture, $CO_2$ is preferably present as at least about 10% of the mixture. The presence of oxygen should be avoided due to the fact that it can affect the yields and present a hazard of combustion. Suitable $CO_2$ pressures are from about 200 to 10,000 psig. Actual pressures depend upon the partial pressures of other gases present. A more preferred $CO_2$ pressure range is from about 200 to 1000 psig. To accelerate the reaction and suppress the occurrence of side reactions the reaction temperature is preferably about 450° C. and the pressure is about 300 psig.

The reaction can optionally be carried out in the presence of other basic salts to further increase the rate of reaction, however this may add to the expense and is not critical to the reaction. Some salts may be thermally stable under the particular conditions used, and may, therefore, if in the molten state, be used as solvents for the reaction, facilitating the interaction of the other components. Basic salts consist of materials such as potassium oxalate, potassium acetate, potassium formate, potassium malonate, potassium sorbate, potassium citrate, dipotassium salicylate, potassium phenolate, potassium resorcinolate, potassium naphtholate, potassium cresolate, dipotassium carbonylate, potassium hydride, and the like. In the above list, "potassium" may be taken as either "monopotassium" or "dipotassium", "tripotassium", etc. up to the limit of available hydroxy (or hydroxy and carboxy groups) according to the particular material. Sodium, cesium, or rubidium can also be used as the counter ion, but potassium is generally preferred due to the best balance of cost and efficacy. If the salt feed is a solid, the reaction of the two solids (salt and base, such as $K_2CO_3$) will normally proceed well under the reaction conditions. The basic carboxylating salts may also be mixed with potassium carbonate, and may be formed by the mixture of the salts with potassium carbonate.

The use of a molten solvent or diluent medium may facilitate transfer of the reacting mass from vessel to vessel and improve mixing, however it is not necessary to the practice of the invention. If a diluent medium is used, it should be liquid, stable at the temperatures employed, and, if inert, a material which does not undesirably affect the reaction.

In another aspect of the invention, where salts are used, they may be in the form of a eutectic mixture. A eutectic mixture provides the lowest melting point of a mixture of two or more alkali metals that is obtainable by varying the percentage of the components. Eutectic mixtures have a definite minimum melting point compared with other combinations of the same metals. For example, though the melting point of $Li_2CO_3$ is 622° C., in a eutectic mixture of alkali carbonates the melting point can be 400° C. What is required where a eutectic mixture is employed, is the right mixture of alkali metal carbonates where the melting point is less than about 400° C. Generally the ratio of alkali metal carbonates in the eutectic mixture is about 1:1:1, but it can vary. One eutectic mixture that can be used as a solvent is $K_2CO_3$, $Rb_2CO_3$, $Cs_2CO_3$, and optionally $Na_2CO_3$.

The following examples will serve to illustrate specific embodiments of the invention disclosed herein. These examples are intended only as a means of illustration and should not be construed as limiting the scope of the invention in any way. Those skilled in the art will recognize many variations that may be made without departing from the spirit of the disclosed invention.

EXAMPLE 1

Potassium phenolate was added to a Henkel reaction of potassium naphthoate and dipotassium K2-2,3 NDA with ZnO catalyst at 450° C. under 500 psig of $CO_2$. Surprisingly, it was observed that the major products were TPA and 2,6-NDA. Since it is impossible to cleave the naphthalene ring to a benzene ring under the reaction conditions, it was apparent that the phenol must have formed TPA in this reaction mixture, contrary to expectation from the literature. Based upon the literature, it was expected that the phenol would form the dipotassium salt of para-hydroxy benzoic acid, and perhaps, due to the high temperature, add a second or third acid group, to make a polyacid capable of transferring acid groups to the naphthoic acid salt. (It has been shown that tricarboxylic benzene acids, but not dicarboxylic, will carboxylate naphthoic acid by transcarboxylation). Therefore it was thought that the yield of naphthoic acid might be increased, based on extrapolation of the known literature information and coupling it with prior research into the Henkel reaction. Instead, the yield of 2,6-NDA was unaffected, and TPA was also observed. Subsequent experiments showed that, contrary to other claims in the literature, K2-TPA salts will not carboxylate naphthoic acid salts. This is reasonable on thermodynamic grounds, due to the very high stability of the TPA structure.

However, the experiment showed that phenol itself is converted to TPA under the reaction conditions.

EXAMPLE 2

A 100 cc hoke vessel fitted with a magnetic stirrer is charged with 50 g of potassium phenolate and an excess of 5 g of potassium carbonate, 5 g of zinc oxide, and pressurized to 250 psig with $CO_2$ several times after warming to ca. 100° C. to purge the air. It is then left pressurized with 250 psig of $CO_2$, sealed, and heated to 450° C. for three hours with stirring. On cooling, it is found that about 4% per hour of the phenolate has been converted to K2-TPA. Some discoloration has occurred, with very minor amounts of condensed aromatic products formed, but practically all of the unconverted phenolate is recovered unreacted. The only significant product observed is terephthalic acid (as the dipotassium salt). The rate of production is slower than that which would have occurred from potassium benzoate via the Henkel reaction (by about a factor of 5) but remarkable in that parahydroxy benzoic acid salt is not present, or only present in trace amounts. Other benzene diacids besides TPA are also only present in very minor amounts. The reaction product is essentially pure K2-TPA in essentially pure potassium phenolate feed.

EXAMPLE 3

The reaction of Example 2 is repeated at 400° C. Very little reaction occurs.

EXAMPLE 4

The reaction is repeated at 550° C. An increased amount of TPA is observed, but there is also a significant amount of condensed ring hydrocarbon decomposition products and benzene.

EXAMPLE 5

The reaction of example 2 is substantially repeated with potassium 2-naphtholate instead of potassium phenolate. Related results, with the formation of a lesser amount of 2,6-NDA and a greater amount of carbonaceous matter and other NDA isomers are observed.

EXAMPLE 6

The experiment of example 2 is substantially repeated without the use of ZnO or $K_2CO_3$. Again TPA is the product formed, but the apparent rate is somewhat reduced. It will be obvious to those skilled in the art that many other modifications of process design, temperature, pressure, and catalyst content will also effect this new reaction. For example, molten phenolate salt might be exposed to high pressure $CO_2$ at high temperature in a wiped film to effect the reaction. The K2-TPA or NDA salt formed might be removed from the molten phenolate or napholate by a filtration step at high temperature instead of by dissolution of the entire mass in water and precipitation with $CO_2$ or other acid. The product salts might also be adsorbed on an adsorbent, such as active carbon, which is known to bind aromatic acid salts. These and many other modifications might be practiced to reduce the cost of isolation of the desired product from the starting materials.

EXAMPLE 7

3.9 g of phenol was heated with 11.2 g of potassium carbonate in the presence of 1.1 g of ZnO at 460° C. with 5 g of naphthalene diluent under $CO_2$. After calcination it is found that the product consists of terephthalic acid, as the dipotassium salt, in a purity of 99.6% plus. No benzene, ketones, or other products can be found in the reaction mixture. Although the yield is 5%, the complete absence of byproducts, and the favorable thermodynamics observed in the process, indicate the likelihood that modifications of conditions, such as, for example, increasing temperature, improving mixing, and pre-forming the potassium phenolate will result in much higher conversions.

We claim:

1. An oxidation free process for converting a hydroxy substituted aromatic, or salt thereof, to an aromatic diacid which comprises reacting said hydroxy substituted aromatic with excess basic salt in the presence of carbon dioxide under disproportionation/isomerization reaction conditions at a temperature in a range of 350 to 500° C.

2. The process of claim 1 wherein the hydroxy substituted aromatic is selected from the group consisting of any of the isomeric hydroxy substituted derivatives of benzene, naphthalene, anthracene, phenanthrene, indene, isoindene, benzofuran, isobenzofuran, indole, 1,2-benzopyran, quinoline, isoquinoline, acenaphthene, fluorene, dibenzopyrrole, xanthene, thianthrene, naphthacene, chrysene, pyrene, triphenylene, and combinations thereof wherein the hydroxyl group is bonded to a nuclear carbon atom.

3. The process of claim 1 wherein said hydroxy substituted aromatic is selected from aryl hydroxy compounds having more than one hydroxyl radical bonded to a nuclear aromatic carbon atom.

4. The process of claim 1 wherein said hydroxy substituted aromatic is selected from phenol and naphthol.

5. The process of claim 1 wherein said basic salt is selected from the group consisting of alkali metal or alkali earth metal carbonates.

6. The process of claim 5 wherein said basic salt is selected from the group consisting of lithium, sodium, potassium, rubidium, and cesium.

7. The process of claim 6 wherein said basic salt is selected from the group consisting of $K_2CO_3$, $KHCO_3$, $Rb_2CO_3$, $RbHCO_3$, $Cs_2CO_3$, $CsHCO_3$, and other strongly basic carbonates or bicarbonates.

8. The process of claim 7 wherein said basic salt is selected from potassium carbonate or potassium bicarbonate.

9. The process of claim 1 further comprising the use of a disproportionation catalyst selected from compounds of Group IB, IIB, VB, or VIIB of the Periodic Table.

10. The process of claim 9 wherein said catalyst is selected from oxides, halides, sulfates, carbonates, and carboxylates of Group IB, IB, VB, or VIIB.

11. The process of claim 10 wherein said catalyst is selected from oxides, halides, sulfates, carbonates, and carboxylates of zinc, cadmium and manganese.

12. The process of claim 11 wherein said catalyst is zinc oxide.

13. The process of claim 9 further comprising the use of one or more basic salts to increase the rate of reaction selected from the group consisting of potassium oxalate, potassium acetate, potassium formate, potassium malonate, potassium sorbate, potassium citrate, potassium salicylate, potassium phenolate, potassium resorcinolate, potassium naphtholate, potassium cresolate, dipotassium carbonylate, potassium hydride, and mixtures thereof.

14. The process of claim 1 wherein said disproportionation/isomerization reaction conditions and pressure in the range of 100–1000 psig.

15. The process of claim 14 wherein said temperature is in range of 420–500° C. and said pressure is in the range of 400–600 psig.

* * * * *